United States Patent [19]

Takatsu et al.

[11] Patent Number: 4,788,363
[45] Date of Patent: Nov. 29, 1988

[54] NEMATIC METHYLTOLANS

[75] Inventors: Haruyoshi Takatsu, Tokyo; Yuji Tamura; Kunihiko Kotani, both of Saitama, all of Japan

[73] Assignee: Dainippon Ink and Chemicals, Inc., Tokyo, Japan

[21] Appl. No.: 74,670

[22] Filed: Jul. 16, 1987

[30] Foreign Application Priority Data

Jul. 17, 1986 [JP] Japan .................. 61-168299

[51] Int. Cl.$^4$ ................ C09K 19/30; C09K 19/54; C07C 13/28
[52] U.S. Cl. ................ 585/20; 252/299.63; 252/299.5; 350/350 R
[58] Field of Search .......... 252/299.63, 299.5; 585/20, 25; 350/350 R

[56] References Cited

U.S. PATENT DOCUMENTS

| | | | |
|---|---|---|---|
| 3,925,482 | 12/1975 | Jacques et al. | 585/25 |
| 4,670,182 | 2/1987 | Fujita et al. | 252/299.63 |
| 4,705,870 | 11/1987 | Takatsu et al. | 252/299.63 |
| 4,705,905 | 11/1987 | Takatsu et al. | 252/299.63 |
| 4,713,468 | 12/1987 | Takatsu et al. | 252/299.63 |

FOREIGN PATENT DOCUMENTS

| | | | |
|---|---|---|---|
| 84194 | 7/1983 | European Pat. Off. | 252/299.6 |
| 2234261 | 2/1975 | France | 252/299.6 |
| 123903 | 9/1981 | Japan | 585/25 |
| 200932 | 9/1986 | Japan | 585/25 |
| 62-103031 | 5/1987 | Japan | 252/299.63 |

Primary Examiner—Teddy S. Gron
Assistant Examiner—J. E. Thomas
Attorney, Agent, or Firm—Armstrong, Nikaido, Marmelstein & Kubovcik

[57] ABSTRACT

A nematic methyltolan of the formula:

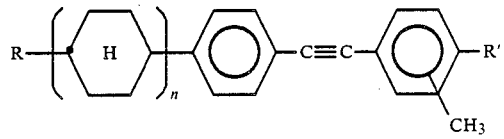

wherein R and R' each represents independently a straight-chained alkyl group with 1 to 9 carbon atoms; n is an integer of 1 or 2; and

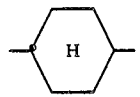

has a trans (equatorial-equatorial) configuration.

13 Claims, No Drawings

NEMATIC METHYLTOLANS

BACKGROUND OF THE INVENTION

The present invention relates to a novel methyltolan type nematic compound useful as an electro-optical display material.

The current market for liquid crystal displays is dominated by TN (twisted nematic) cells which fall under the category of field-effect cells. As reported by G. Bauer in Mol. Cryst. Liq. Cryst. 63, 45 (1981), these TN cells produce interference patterns on the cell surface that can impair the appearance of the cell and in order to prevent the occurrence of such patterns, the product of birefringence ($\Delta_n$), of the refractive index of liquid crystal material in the cell and the cell thickness, d ($\mu$m), must be fixed to a specified value. In commercial liquid display cells, the product $\Delta_n \cdot d$ is fixed to one of the values 0.5, 1.0, 1.6 and 2.2. Since the value of $\Delta_n \cdot d$ may be fixed to the specified value, the use of a liquid crystal marerial having a large value of $\Delta_n$ will lead to a decrease in d. If d is small, the response time of the cell is shortened in accordance with the well known relation $\tau \alpha d^2$. Therefore, a liquid crystal material having a large value of $\Delta_n$ is of vital importance in the fabrication of a liquid crystal display cell that features quick response and the absence of any interference patterns.

Many of the commercially feasible liquid crystal materials available today are usually prepared by mixing a few or more components made of a compound that has a nematic phase at or near room temperature and a compound that has a nematic phase in ranges higher than room temperature. Most of these mixed liquid crystals commercially used today are required to have a nematic phase over the full temperature range of $-30°$ to $+65°$ C. As the application of liquid crystal display cells increases in diversity, it is desired to develop liquid crystal materials of large $\Delta_n$ that have a nematic phase in an even higher temperature range and to this end, nematic liquid crystal compounds having large $\Delta_n$ with high nematic to isotropic (N-I) transition temperatures are required.

With a view to meeting this need, the present inventors previously proposed

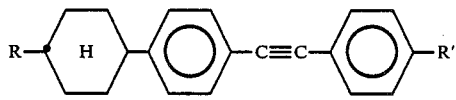

as a nematic liquid crystal compound having a large $\Delta_n$ and a high N-I transition temperature (Japanese Patent Application (OPI) No. 152427/85 corresponding to Ser. No. 692,570 now abandoned) (the term "OPI" as used herein refers to a "published unexamined Japanese patent application"). However, as it turned out, this compound is not high in miscibility with the nematic mixed liquid crystals commonly used today, especially at low temperatures.

SUMMARY OF THE INVENTION

A principal object, therefore, of the present invention is to provide a novel nematic liquid crystal compound that has a large $\Delta_n$, a high N-I transition temperature and good miscibility at low temperatures with the nematic mixed liquid crystals in common use today.

This object can be obtained by a compound of the following formula:

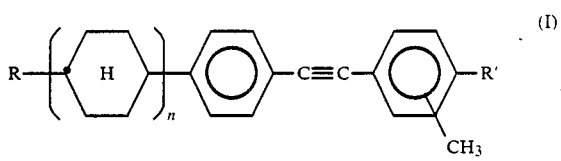

wherein R and R' each represents independently a straight-chained alkyl group with 1 to 9 carbon atoms; n is an integer of 1 or 2; and

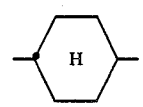

has a trans (equatorialequatorial) configuration.

DETAILED DESCRIPTION OF THE INVENTION

The compound (I) of the present invention can be produced by the following reaction scheme, in which R and n in formula (II) and R' in formula (III) have the same meanings as defined for formula (I):

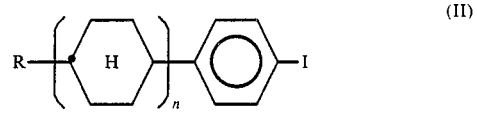

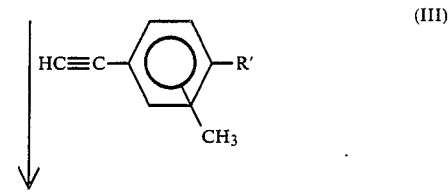

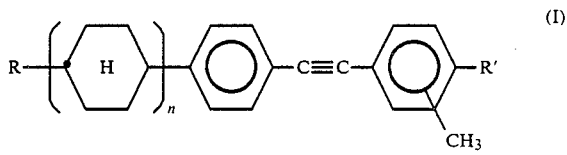

The compound of formula (II) is reacted with the compound of formula (III) in a solvent such as N,N-dimethylformamide in the presence of bis(triphenylphosphine) palladium (II) chloride and cuprous iodide as catalysts, so as to produce the compound of formula (I) of the present invention.

The transition temperatures of typical compounds of formula (I) produced by this method are noted in Table 1 below.

TABLE 1

R−(H)ₙ−⟨○⟩−C≡C−⟨○⟩−R'
                              |
                              CH₃

| No. | R | R' | n | Transition temperature (°C.) |
|---|---|---|---|---|
| 1 | n-C₃H₇— | —CH₃ | 1 | 77 (C →N)* |
|   |   |   |   | 174 (N ←I) |
| 2 | n-C₄H₉— | —CH₃ | 1 | 65 (C →N) |
|   |   |   |   | 163 (N ←I) |
| 3 | n-C₄H₉— | —CH₃ | 2 | 125 (C →S) |
|   |   |   |   | 162 (S →N) |
|   |   |   |   | >300 (N ←I) |

*Remarks:
C: crystalline phase;
N: nematic phase;
I: isotropic liquid phase;
S: smectic phase.

The compounds of formula (I) of the present invention are nematic liquid crystal compounds having a weak positive or negative value of anisotropy in dielectric constant. Therefore, if they are mixed with other nematic liquid crystal compounds having negative anisotropy in dielectric constant, materials suitable for use in dynamic scattering mode display cells can be produced. If the compounds of formula (I) are mixed with the other nematic liquid crystal compounds having positive or negative anisotropy in dielectric constant, materials suitable for use in twisted-nematic display cells may be obtained.

Illustrative compounds that can be mixed with the compounds of formula (I) to make preferable materials for use in liquid crystal display cells are listed below: 4'-substituted phenyl 4-substituted benzoate, 4'-substituted phenyl 4-substituted cyclohexanecarboxylate, 4'-substitued biphenyl 4-substituted cryclohexanecarboxylate, 4'-substituted phenyl 4-(4-substituted cyclohexanecarbonyloxy)benzoate, 4'-substituted phenyl 4-(4-substituted cyclohexyl)benzoate, 4'-substituted cyclohexyl 4-(4-substituted cyclohexyl)benzoate, 4-substituted 4'-substituted biphenyl, 4-substituted 4'-substituted cylohexane, 4-substituted 4'-substituted terphenyl, 4-substituted biphenyl 4'-substituted cyclohexane, and 2-(4-substituted phenyl)-5-substituted pyrimidine.

Table 2 lists the N-I transition temperature and birefringences (Δₙ) of mixed liquid crystals composed of 85 wt% of liquid-crystal host (A) and 15 wt% of compound No. 1, 2 or 3 of formula (I) shown in Table 1. Table 2 also shows the N-I transition temperature and Δₙ of liquid-crystal host (A) for comparison. Liquid-crystal host (A) is currently in extensive use as a nematic liquid crystal material and is composed of the following components:

n-C₃H₇—⟨H⟩—⟨○⟩—CN    20 wt % n-C₅H₁₁—⟨H⟩—⟨○⟩—CN    16 wt % n-C₇H₁₅—⟨H⟩—⟨○⟩—CN    16 wt % n-C₃H₇—⟨H⟩—COO—⟨○⟩—OC₂H₅    8 wt % n-C₃H₇—⟨H⟩—COO—⟨○⟩—O—n-C₄H₉    8 wt % n-C₄H₉—⟨H⟩—COO—⟨○⟩—OCH₃    8 wt % n-C₄H₉—⟨H⟩—COO—⟨○⟩—OC₂H₅    8 wt % n-C₅H₁₁—⟨H⟩—COO—⟨○⟩—OCH₃    8 wt % n-C₅H₁₁—⟨H⟩—COO—⟨○⟩—OC₂H₅    8 wt %

TABLE 2

|  | N-I transition temperature (°C.) | Δₙ (—) |
|---|---|---|
| (A) | 54.0 | 0.0917 |
| (A) + No. 1 | 70.8 | 0.116 |
| (A) + No. 2 | 69.3 | 0.115 |
| (A) + No. 3 | 90.9 | 0.113 |

One will understand from Table 2 that compounds of formula (I) increase the N-I transition temperature of the liquid-crystal host to levels that are satisfactory for practical applications and that they also achieve significant increases in Δₙ.

These advantages of the present invention will also become apparent from the following comparative experiment. A known compound having the formula:

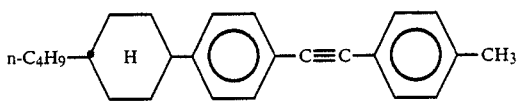

which is similar to formula (I) was developed with a view to increasing the N-I transition temperature and $\Delta_n$ of a mixed liquid crystal. This compound had 6% solubility in liquid-crystal host (A) at $-30°$ C. The resulting mixed liquid crystal had a N-I transition point of 62.1° C. and $\Delta_n$ of 0.01. In contrast, compound No. 2 of the present invention having the formula:

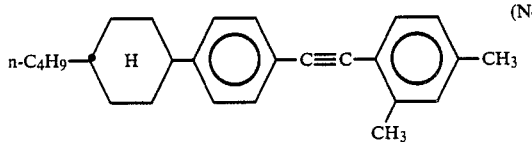

had 13% solubility in liquid-crystal host (A) at $-30°$ C., and the resulting mixed liquid crystal had a N-I transition point of 67.2° C. and $\Delta_n$ of 0.112.

These results suggest that compounds of formula (I) within the scope of the present invention which can be incorporated in a liquid-crystal host in greater amounts than a representative known analogous compound and are effective in achieving marked increases in the N-I transition temperature and $\Delta_n$ of the mixed liquid crystal.

The following examples are provided for the purpose of further illustrating the present invention but are in no way to be taken as limiting.

EXAMPLE 1

A compound of the formula

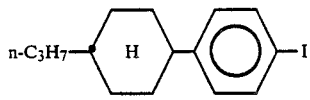

was dissolved in 400 ml of N,N-dimethylformamide in an amount of 39.6 g (0.120 mol). To the resulting solution were added 240 mg (0.34 mmol) of bis(triphenylphosphine) palladium (II) chloride, 600 mg (3.1 mmol) of cuprous iodide and 100 ml of diethylamine. To the mixture, 15.6 g (0.120 mol) of 2,4-dimethylphenylacetylene was added with stirring. The resulting mixture was reacted at room temperature for 20 hours. The reaction mixture was rendered acidic by being added to a cold dilute aqueous solution of hydrogen chloride (HCl) with stirring. The reaction product was extracted with toluene and the extract was washed with water, dried and freed of toluene by distillation.

The recovered reaction product was recrystallized from ethyl acetate to obtain 28.5 g (0.0828 mol) of the following compound in pure form:

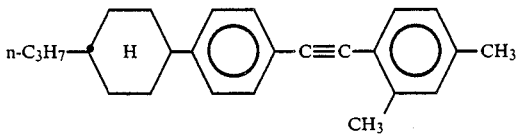

Yield: 69.0%

Transition temperature: 77° C. (C→N); 174° C. (N⇌I).

By similar procedures, the following compound was obtained:

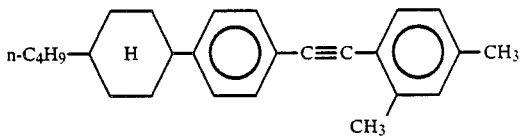

Yield: 67.1

Transition temperature: 65° C. (C→N); 163° C. (N⇌I).

Additional compounds that can be produced by similar procedures are listed in Table 3.

Among the compounds listed in Table 3, those wherein R' is a methyl group are preferred.

TABLE 3

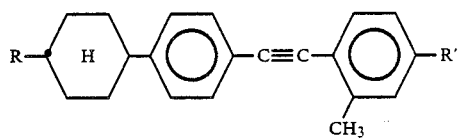

| No. | R | R' |
|---|---|---|
| 4 | $CH_3-$ | $-CH_3$ |
| 5 | $C_2H_5-$ | $-CH_3$ |
| 6 | $n-C_5H_{11}-$ | $-CH_3$ |
| 7 | $n-C_6H_{13}-$ | $-CH_3$ |
| 8 | $n-C_7H_{15}-$ | $-CH_3$ |
| 9 | $n-C_8H_{17}-$ | $-CH_3$ |
| 10 | $n-C_9H_{19}-$ | $-CH_3$ |
| 11 | $CH_3-$ | $-C_2H_5$ |
| 12 | $C_2H_5-$ | $-C_2H_5$ |
| 13 | $n-C_3H_7-$ | $-C_2H_5$ |
| 14 | $n-C_4H_9-$ | $-C_2H_5$ |
| 15 | $n-C_5H_{11}-$ | $-C_2H_5$ |
| 16 | $n-C_6H_{13}-$ | $-C_2H_5$ |
| 17 | $n-C_7H_{15}-$ | $-C_2H_5$ |
| 18 | $n-C_8H_{17}-$ | $-C_2H_5$ |
| 19 | $n-C_9H_{19}-$ | $-C_2H_5$ |
| 20 | $CH_3-$ | $-n-C_3H_7$ |
| 21 | $C_2H_5-$ | $-n-C_3H_7$ |
| 22 | $n-C_3H_7-$ | $-n-C_3H_7$ |
| 23 | $n-C_4H_9-$ | $-n-C_3H_7$ |
| 24 | $n-C_5H_{11}-$ | $-n-C_3H_7$ |
| 25 | $n-C_6H_{13}-$ | $-n-C_3H_7$ |
| 26 | $n-C_7H_{15}-$ | $-n-C_3H_7$ |
| 27 | $n-C_8H_{17}-$ | $-n-C_3H_7$ |
| 28 | $n-C_9H_{19}-$ | $-n-C_3H_7$ |
| 29 | $CH_3-$ | $-n-C_4H_9$ |
| 30 | $C_2H_5-$ | $-n-C_4H_9$ |
| 31 | $n-C_3H_7-$ | $-n-C_4H_9$ |
| 32 | $n-C_4H_9-$ | $-n-C_4H_9$ |
| 33 | $n-C_5H_{11}-$ | $-n-C_4H_9$ |
| 34 | $n-C_6H_{13}-$ | $-n-C_4H_9$ |
| 35 | $n-C_7H_{15}-$ | $-n-C_4H_9$ |
| 36 | $n-C_8H_{17}-$ | $-n-C_4H_9$ |
| 37 | $n-C_9H_{19}-$ | $-n-C_4H_9$ |
| 38 | $CH_3-$ | $-n-C_5H_{11}$ |
| 39 | $C_2H_5-$ | $-n-C_5H_{11}$ |
| 40 | $n-C_3H_7-$ | $-n-C_5H_{11}$ |
| 41 | $n-C_4H_9-$ | $-n-C_5H_{11}$ |
| 42 | $n-C_5H_{11}-$ | $-n-C_5H_{11}$ |
| 43 | $n-C_6H_{13}-$ | $-n-C_5H_{11}$ |
| 44 | $n-C_7H_{15}-$ | $-n-C_5H_{11}$ |
| 45 | $n-C_8H_{17}-$ | $-n-C_5H_{11}$ |
| 46 | $n-C_9H_{19}-$ | $-n-C_5H_{11}$ |
| 47 | $CH_3-$ | $-n-C_6H_{13}$ |
| 48 | $C_2H_5-$ | $-n-C_6H_{13}$ |
| 49 | $n-C_3H_7-$ | $-n-C_6H_{13}$ |
| 50 | $n-C_4H_9-$ | $-n-C_6H_{13}$ |
| 51 | $n-C_5H_{11}-$ | $-n-C_6H_{13}$ |

TABLE 3-continued

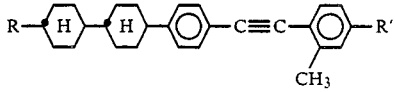

| No. | R | R' |
|---|---|---|
| 52 | n-C$_6$H$_{13}$— | —n-C$_6$H$_{13}$ |
| 53 | n-C$_7$H$_{15}$— | —n-C$_6$H$_{13}$ |
| 54 | n-C$_8$H$_{17}$— | —n-C$_6$H$_{13}$ |
| 55 | n-C$_9$H$_{19}$— | —n-C$_6$H$_{13}$ |
| 56 | CH$_3$— | —n-C$_7$H$_{15}$ |
| 57 | C$_2$H$_5$— | —n-C$_7$H$_{15}$ |
| 58 | n-C$_3$H$_7$— | —n-C$_7$H$_{15}$ |
| 59 | n-C$_4$H$_9$— | —n-C$_7$H$_{15}$ |
| 60 | n-C$_5$H$_{11}$— | —n-C$_7$H$_{15}$ |
| 61 | n-C$_6$H$_{13}$— | —n-C$_7$H$_{15}$ |
| 62 | n-C$_7$H$_{15}$— | —n-C$_7$H$_{15}$ |
| 63 | n-C$_8$H$_{17}$— | —n-C$_7$H$_{15}$ |
| 64 | n-C$_9$H$_{19}$— | —n-C$_7$H$_{15}$ |
| 65 | CH$_3$— | —n-C$_8$H$_{17}$ |
| 66 | C$_2$H$_5$— | —n-C$_8$H$_{17}$ |
| 67 | n-C$_3$H$_7$— | —n-C$_8$H$_{17}$ |
| 68 | n-C$_4$H$_9$— | —n-C$_8$H$_{17}$ |
| 69 | n-C$_5$H$_{11}$— | —n-C$_8$H$_{17}$ |
| 70 | n-C$_6$H$_{13}$— | —n-C$_8$H$_{17}$ |
| 71 | n-C$_7$H$_{15}$— | —n-C$_8$H$_{17}$ |
| 72 | n-C$_8$H$_{17}$— | —n-C$_8$H$_{17}$ |
| 73 | n-C$_9$H$_{19}$— | —n-C$_8$H$_{17}$ |
| 74 | CH$_3$— | —n-C$_9$H$_{19}$ |
| 75 | C$_2$H$_5$— | —n-C$_9$H$_{19}$ |
| 76 | n-C$_3$H$_7$— | —n-C$_9$H$_{19}$ |
| 77 | n-C$_4$H$_9$— | —n-C$_9$H$_{19}$ |
| 78 | n-C$_5$H$_{11}$— | —n-C$_9$H$_{19}$ |
| 79 | n-C$_6$H$_{13}$— | —n-C$_9$H$_{19}$ |
| 80 | n-C$_7$H$_{15}$— | —n-C$_9$H$_{19}$ |
| 81 | n-C$_8$H$_{17}$— | —n-C$_9$H$_{19}$ |
| 82 | n-C$_9$H$_{19}$— | —n-C$_9$H$_{19}$ |

EXAMPLE 2

The procedures of Example 1 were repeated except that the compound of the formula

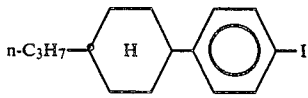

was replaced by 50.9 g (0.120 mol) of a compound of the formula

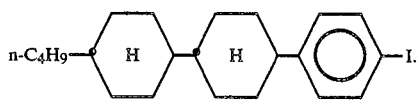

The compound thus obtained had the following formula:

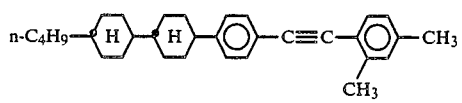

Yield: 64.1%

Transition temperature: 125° C. (C→S); 162° C. (S⇌N); <300° C. (N⇌I).

By similar procedures, a variety of compounds having the general formula

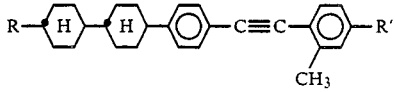

can be produced. In this formula, R and R' may be combined in any of the ways that are specifically indicated in Example 1.

By repeating the procedures of Example 1 except that 2,4-di-methylphenylacetylene was replaced by a 3,4-dimethylphenylacetylene having the general formula

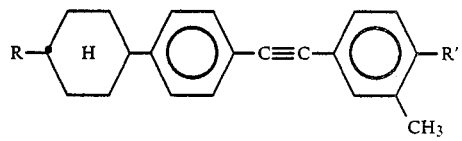

can be produced. In this formula, R and R' may be combined in any of the ways that are specifically indicated in Example 1.

By repeating the procedures of Example 1 except that the compound of the formula

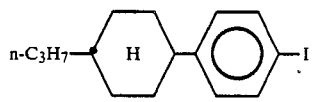

was replaced by a compound of the formula

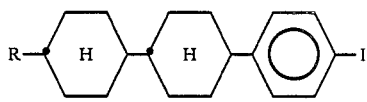

and that 2,4-dimethylphenylacetylene was replaced by a 3-methyl-4-alkylphenylacetylene, compounds of the general formula

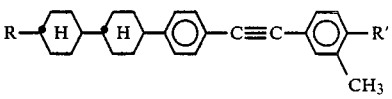

could be produced. In this formula, R and R' may be combined in any of the ways that are specifically indicated in Example 1.

The novel nematic liquid crystal compound of the present invention has a high N-I transition temperature and a large $\Delta_n$ as well. Therefore, the N-I transition temperature and $\Delta_n$ of a known mixed liquid crystal can be increased by mixing it with the compound of the present invention. In addition, compared with a known structural temperature and $\Delta_n$ of a known mixed liquid crystal can be increased by mixing it with the compound of the present invention. In addition, compared with a known structurally analogous compound, the compound of the present invention has a great solubility in known mixed liquid crystals at low temperatures and, hence, mixed liquid crystals having even higher N-I transition temperatures and $\Delta_n$ values can be prepared.

While the invention has been described in detail and with reference to specific embodiments thereof, it will be apparent to one skilled in the art that various changes and modifications can be made therein without departing from the spirit and scope thereof.

What is claimed is:

1. A compound of the general formula:

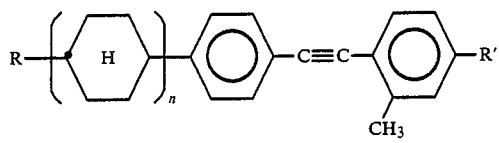

wherein R and R' each independently represent a straight-chained alkyl group with 1 to 9 carbon atoms; n is an integer of 1 or 2; and

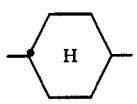

has a trans (equatorial-equatorial) configuration.

2. The compound of claim 1, wherein the compound is represented by formula:

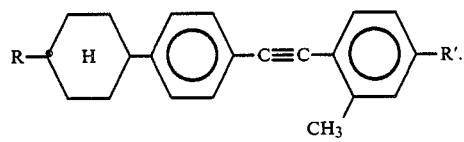

3. The compound of claim 1, wherein the compound is represented by formula:

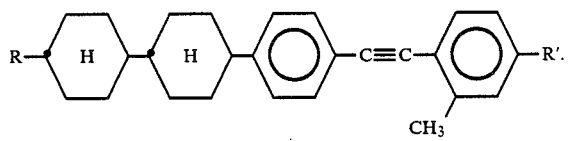

4. The compound of claim 1, wherein the compound is represented by formula:

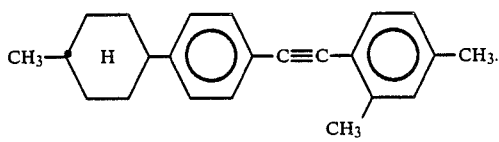

5. The compound of claim 1, wherein the compound is represented by formula:

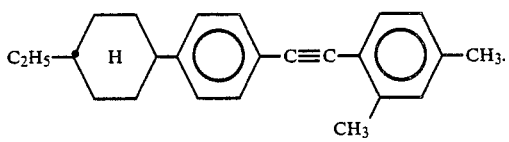

6. The compound of claim 1, wherein the compound is represented by formula:

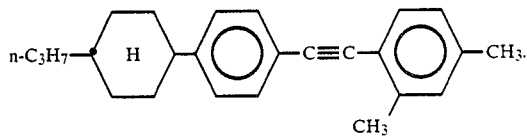

7. The compound of claim 1, wherein the compound is represented by formula:

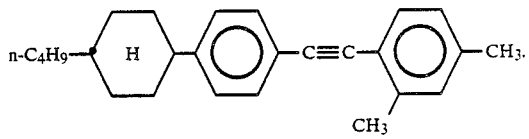

8. The compound of claim 1, wherein the compound is represented by formula:

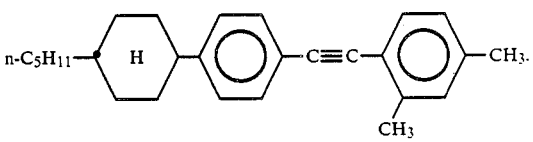

9. The compound of claim 1, wherein the compound is represented by formula:

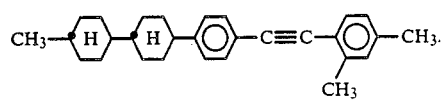

10. The compound of claim 1, wherein the compound is represented by formula:

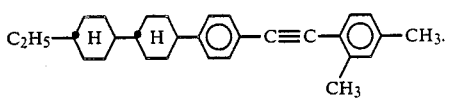

11. The compound of claim 1, wherein the compound is represented by formula:

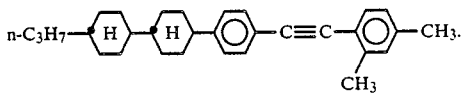

12. The compound of claim 1, wherein the compound is represented by formula:

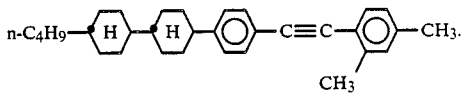

13. The compound of claim 1, wherein the compound is represented by formula:

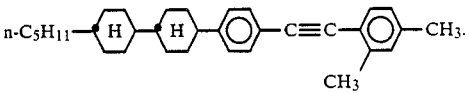

* * * * *